(12) United States Patent
Wang et al.

(10) Patent No.: US 10,047,063 B2
(45) Date of Patent: *Aug. 14, 2018

(54) METHOD FOR IMPROVING THE OXYGEN-RELEASING ABILITY OF HEMOGLOBIN TO ORGANS OR PERIPHERAL TISSUES IN HUMAN BODIES AND A MEDICATION THEREOF

(71) Applicant: NATIONAL SUN YAT-SEN UNIVERSITY, Kaohsiung (TW)

(72) Inventors: Chia-Chen Wang, Kaohsiung (TW); Muhammad Zulfajri, Kaohsiung (TW); You-Qing Yu, Kaohsiung (TW)

(73) Assignee: NATIONAL SUN YAT-SEN UNIVERSITY, Kaohsiung (TW)

(*) Notice: Subject to any disclaimer, the term of this patent is extended or adjusted under 35 U.S.C. 154(b) by 20 days.

This patent is subject to a terminal disclaimer.

(21) Appl. No.: 15/411,637

(22) Filed: Jan. 20, 2017

(65) Prior Publication Data

US 2017/0129866 A1    May 11, 2017

Related U.S. Application Data

(63) Continuation-in-part of application No. 14/738,381, filed on Jun. 12, 2015, now abandoned.

(30) Foreign Application Priority Data

Sep. 1, 2014 (TW) .............................. 103130165 A

(51) Int. Cl.
| | | |
|---|---|---|
| C07D 493/04 | (2006.01) | |
| C07D 307/87 | (2006.01) | |
| C07D 307/77 | (2006.01) | |

(52) U.S. Cl.
CPC ......... *C07D 307/87* (2013.01); *C07D 307/77* (2013.01); *C07D 493/04* (2013.01)

(58) Field of Classification Search
CPC ................................................... C07D 493/04
See application file for complete search history.

(56) References Cited

FOREIGN PATENT DOCUMENTS

| | | |
|---|---|---|
| TW | 20101815 | 6/2010 |
| TW | M404712 U1 | 6/2011 |

OTHER PUBLICATIONS

Lao et al, "Identification and quantification of 13 compounds in *Angelica sinensis* (Danggui) by gas chromatography-mass spectrometry coupled with pressurized liquid extraction", Analytica Chima Acta, 2004, 526, pp. 131-137.

*Primary Examiner* — Noble E Jarrell
*Assistant Examiner* — John S Kenyon
(74) *Attorney, Agent, or Firm* — Muncy, Geissler, Olds & Lowe, P.C.

(57) ABSTRACT

A method for improving the oxygen-releasing ability of hemoglobin, hemoglobin variants, recombinant hemoglobin or hemoglobin-based blood substitutes to organs or peripheral tissues in human bodies is disclosed by administering a compound of phthalides to a subject in need thereof. The compound of phthalides is characterized by a phthalide functional group which is represented as Formula I, and forms at least one hydrogen bond with αArg141 of hemoglobin, hemoglobin variants, recombinant hemoglobin or hemoglobin-based blood substitutes, stabilizing the α1/α2 interface of hemoglobin, further stabilizing the oxygenated hemoglobin, hemoglobin variants, recombinant hemoglobin or hemoglobin-based blood substitutes in the low oxygen affinity "T" state and facilitating the oxygen release to the organs or the peripheral tissues. A medication for improving the oxygen-releasing ability of hemoglobin, hemoglobin variants, recombinant hemoglobin, or hemoglobin-based blood substitutes to organs or peripheral tissues in human bodies is also disclosed.

13 Claims, 21 Drawing Sheets

METHOD FOR IMPROVING THE OXYGEN-RELEASING ABILITY OF HEMOGLOBIN TO ORGANS OR PERIPHERAL TISSUES IN HUMAN BODIES AND A MEDICATION THEREOF

CROSS-REFERENCE TO RELATED APPLICATIONS

This application is a Continuation-in-part of the U.S. patent application Ser. No. 14/738,381 filed on Jun. 12, 2015 for which priority is claimed under 35 U.S.C. § 120; and this application claims priority of Application No. 103130165 filed in Taiwan on Sep. 1, 2014 under 35 U.S.C. § 119 and the entire contents of all of which is incorporated herein by reference in its entirety.

Although incorporated by reference in its entirety, no arguments or disclaimers made in the parent application apply to this Continuation-in-part application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention generally relates to a method and, more particularly, to a method for improving the oxygen-releasing ability of hemoglobin (Hb), hemoglobin variants, recombinant hemoglobin or hemoglobin-based blood substitutes to organs or peripheral tissues in human bodies. The present invention further relates to a medication for improving the oxygen-releasing ability of hemoglobin, hemoglobin variants, recombinant hemoglobin or hemoglobin-based blood substitutes to organs or peripheral tissues in human bodies.

BACKGROUND OF THE INVENTION

Hemoglobin is the oxygen-transport protein in the red blood cells. Hemoglobin in the blood carries oxygen from the respiratory organs (i.e. respiratory tract and lung) to organs and peripheral tissues to provide oxygen to the organs and the peripheral tissues and by doing so to assure normal physiological functions of the organs and the peripheral tissues.

In normal adult humans, hemoglobin is a hetero-tetramer, consisting of a pair of dissimilar subunits, including $\alpha_1$, $\alpha_2$, $\beta_1$ and $\beta_2$ subunits. While the backbone amino acid sequence determines the primary structure of each subunit, the intra-subunit hydrogen bonds and salt bridges formed within each of the subunits govern the secondary and tertiary structure of the subunits. Moreover, the inter-subunit hydrogen bonds and salt bridges formed between different subunits determine and regulate the quaternary structure of the tetrameric hemoglobin.

The quaternary structure of hemoglobin may exist in two allosteric conformation states, including a high oxygen affinity relaxed state ("R" state) and a low oxygen affinity tensed state ("T" state). Hemoglobin can bind oxygen and transform to the "R" state when transported to lungs where the partial pressure of oxygen $PO_2$ is high, and release the bound oxygen to the organs and the peripheral tissues where the partial pressure of oxygen $PO_2$ is low, and transform to the "T" state. A number of heterotropic effectors such as pH value, $CO_2$ and 2,3-bisphosphoglycerate (2,3-BPG) play important roles in regulating the allosteric property of hemoglobin. Moreover, there are six inter-subunit hydrogen bonds in hemoglobin being capable of stabilizing hemoglobin in the low oxygen affinity "T" state, including $\alpha_1$Arg141---$\alpha_2$Asp126, $\alpha_1$Arg141---$\alpha_2$Lys127, $\alpha_1$Asp126---$\alpha_2$Arg141, $\alpha_1$Lys127---$\alpha_2$Arg141, $\beta_1$His146---$\alpha_2$Lys40 and $\beta_2$His146---$\alpha_1$Lys40. Among these six "T" state stabilizing inter-subunit contacts, four are related to $\alpha$Arg141 of hemoglobin, pointing to the crucial importance of this residue in sustaining the "T" state.

In general, hemoglobin with an impaired ability of carrying or releasing oxygen may cause a variety of syndromes such as anemia and dizziness; fatigue, weakness and shortness of breath are also frequently found in patients whose hemoglobin has defect oxygen-releasing capability. Syndromes, such as migraine, menstrual disorder and dysmenorrhea are also related with impaired oxygen-delivery efficiency of hemoglobin. Furthermore, insufficient oxygen uptake results in metabolism abnormality and dysfunction of the organs and the peripheral tissues, from which various diseases can begin to develop, including, but not limited to, hypertensions, cardiovascular and neurodegenerative diseases, and growth of carcinogenic cells. The conventional method broadly adopted to treat anemia involves transfusion of normal functional blood. However, this is a passive way of treatment and additional treatments must always be accompanied to alleviate the accompanying adverse side effects. For example, the iron-chelating agent must be applied to patients receiving the blood transfusion in order to down-regulate the iron level in blood to prevent iron-poisoning. In light of this, it is necessary to develop new strategies to improve the oxygen-releasing ability of hemoglobin to the organs and the peripheral tissues in human bodies and to treat various syndromes and diseases related with deficient oxygen delivery. Furthermore, many hemoglobin variants have reduced oxygen delivery capacity when compared with normal hemoglobin, which is often due to the altered allosteric properties or the loss of ability to interact with the endogenous allosteric effector, 2,3-bisphosphoglycerate as a result of structural modification. It is therefore also important to develop a new method to enhance the oxygen delivery ability of hemoglobin variants, recombinant hemoglobin or certain hemoglobin-based blood substitutes for the medical purposes.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 1l is a diagram illustrating the chemical structure of 6,7-epoxyligustilide of the invention.

Figure 1A:
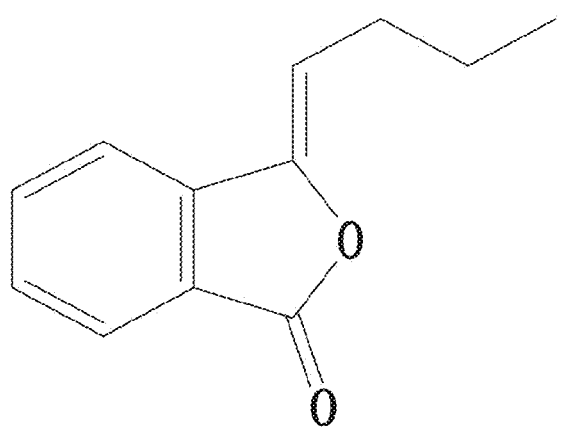
FIG. 1a is a diagram illustrating the chemical structure of Z-butylidenephthalide of the invention.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

SUMMARY OF THE INVENTION

It is therefore the objective of this invention to provide a method for improving the oxygen-releasing ability of hemoglobin, hemoglobin variants, recombinant hemoglobin or hemoglobin-based blood substitutes to organs or peripheral tissues in human bodies, with a compound of Formula I used as the active ingredients for improving the oxygen-releasing ability of hemoglobin, hemoglobin variants, recombinant hemoglobin or hemoglobin-based blood substitutes to the organs or the peripheral tissues in human bodies,

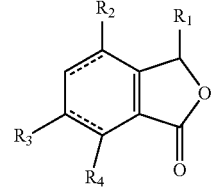

Formula I wherein $R_1$ is $C_2$-$C_6$ alkyl, $C_2$-$C_6$ alkenyl or $C_2$-$C_6$ alkenol group; $R_2$ is one or more H or OH; and $R_3$ and $R_4$ are each independent H or OH or both of them combine together to form a epoxy group.

It is another objective of this invention to provide a medication for improving the oxygen-releasing ability of hemoglobin, hemoglobin variants, recombinant hemoglobin or hemoglobin-based blood substitutes to organs or peripheral tissues in human bodies, with the compound of Formula I used as the active ingredients.

One embodiment of the invention discloses a method for improving the oxygen-releasing ability of hemoglobin, hemoglobin variants, recombinant hemoglobin or hemoglobin-based blood substitutes to organs or peripheral tissues in human bodies, by administering a compound of Formula I to a subject in need thereof to improve the oxygen-releasing ability of hemoglobin, hemoglobin variants, recombinant hemoglobin or hemoglobin-based blood substitutes to the organs or the peripheral tissues in human bodies, wherein the compound of Formula I is:

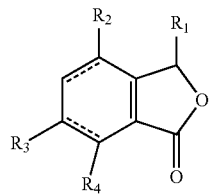

wherein $R_1$ is $C_2$-$C_6$ alkyl, $C_2$-$C_6$ alkenyl or $C_2$-$C_6$ alkenol group; $R_2$ is one or more H or OH; and $R_3$ and $R_4$ are each independent H or OH or both of them combine together to form a epoxy group, wherein Formula I forms at least one hydrogen bond with αArg141 of hemoglobin, hemoglobin variants, recombinant hemoglobin or hemoglobin-based blood substitutes, stabilizing the $α_1/α_2$ interface of hemoglobin, hemoglobin variants, recombinant hemoglobin or hemoglobin-based blood substitutes, thus stabilizing the oxygenated hemoglobin, hemoglobin variants, recombinant hemoglobin or hemoglobin-based blood substitutes in the low oxygen affinity "T" state and by doing so facilitating the oxygen release to the organs or the peripheral tissues.

The other embodiment of the invention discloses a medication for improving the oxygen-releasing ability of hemoglobin, hemoglobin variants, recombinant hemoglobin or hemoglobin-based blood substitutes to organs or peripheral tissues in human bodies, which comprises the compound of Formula I, ferulic acid and 2,3-bisphosphoglycerate (2,3-BPG).

DETAIL DESCRIPTION OF THE INVENTION

Unless otherwise specified, "a" or "an" means "one or more".

A compound of phthalides according to the preferred teachings of the invention is able to form at least one hydrogen bond with αArg141 of hemoglobin, hemoglobin variants, recombinant hemoglobin and hemoglobin-based blood substitute, stabilizing the α1/α2 interface of hemoglobin, further stabilizing the oxygenated hemoglobin, hemoglobin variants, recombinant hemoglobin and hemoglobin-based blood substitute in the low oxygen affinity "T" state and facilitating the oxygen release to organs and peripheral tissues. In detail, the compound of phthalides is any compound that is characterized by a phthalide functional group, which is represented as Formula I:

Formula I

Figure 1B:
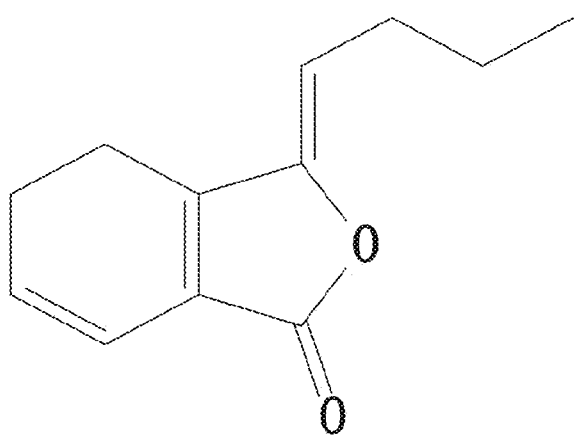
FIG. 1b is a diagram illustrating the chemical structure of Z-ligustilide of the invention.
Figure 1C:
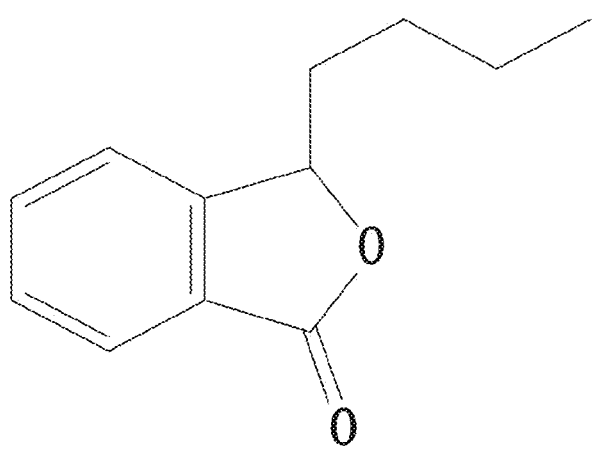
FIG. 1c is a diagram illustrating the chemical structure of senkyunolide A of the invention.
Figure 1D:
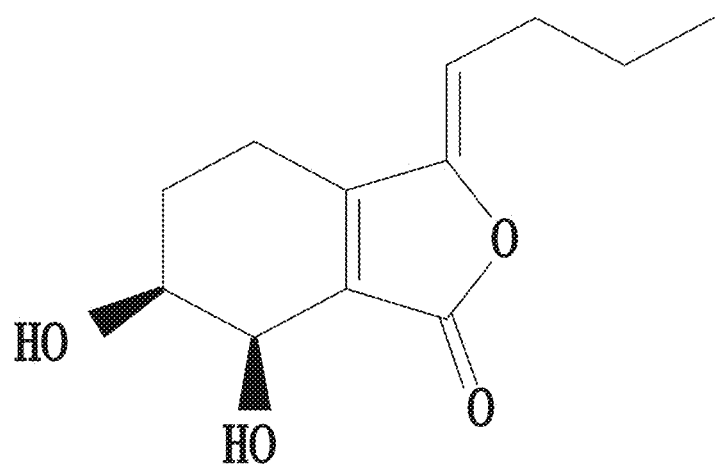
FIG. 1d is a diagram illustrating the chemical structure of senkyunolide H of the invention.
Figure 1E:
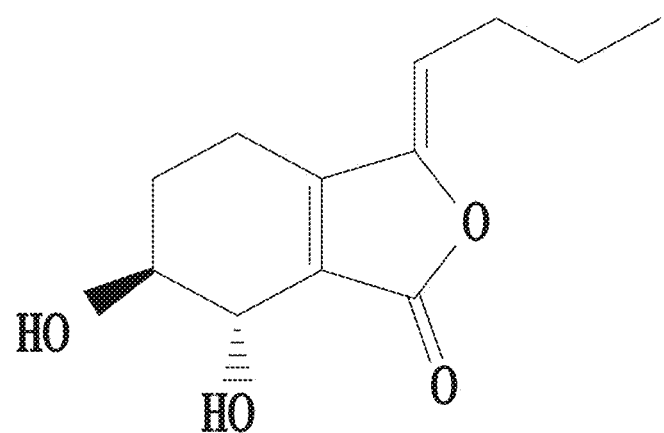
FIG. 1e is a diagram illustrating the chemical structure of senkyunolide I of the invention.
Figure 1F:
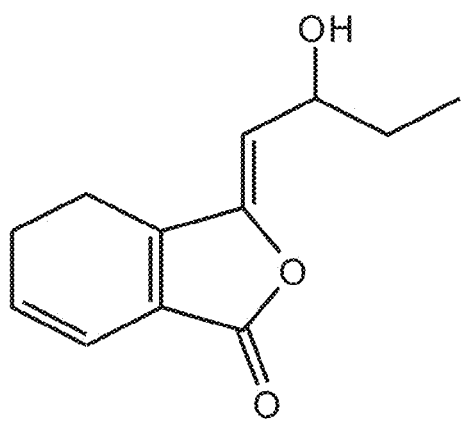
FIG. 1f is a diagram illustrating the chemical structure of senkyunolide F of the invention.
Figure 1G:
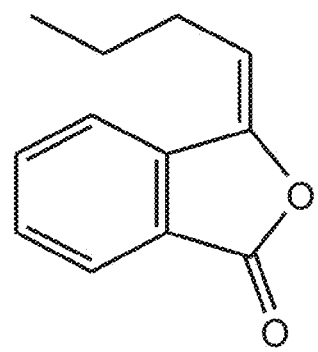
FIG. 1g is a diagram illustrating the chemical structure of E-butylidenephthalide of the invention.
Figure 1H:
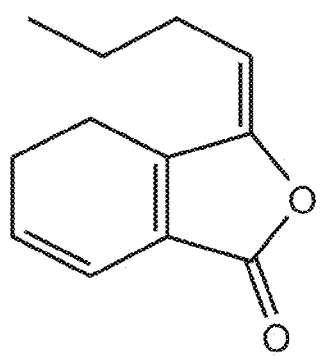
FIG. 1h is a diagram illustrating the chemical structure of E-ligustilide of the invention.
Figure 1I:
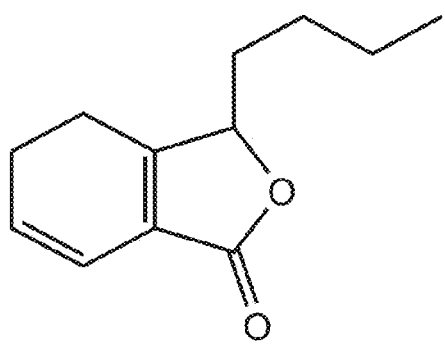
FIG. 1i is a diagram illustrating the chemical structure of 3-butylphthalide of the invention.
Figure 1J:
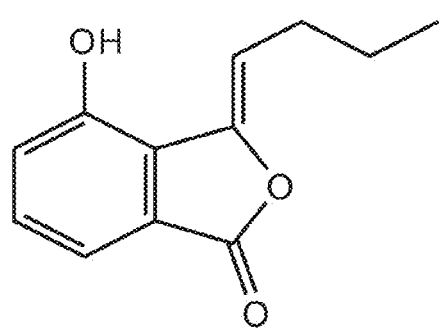
FIG. 1j is a diagram illustrating the chemical structure of 3-butylidene-4-hydrophthalide of the invention.
Figure 1K:
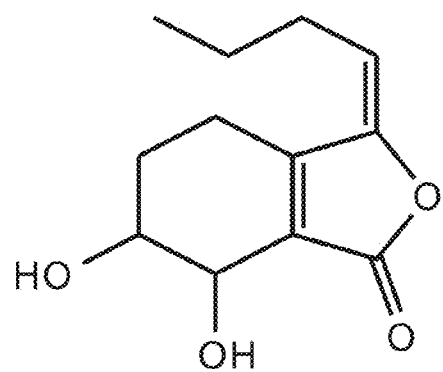
FIG. 1k is a diagram illustrating the chemical structure of 6,7-dihydroxyligustilide of the invention.
Figure 11:
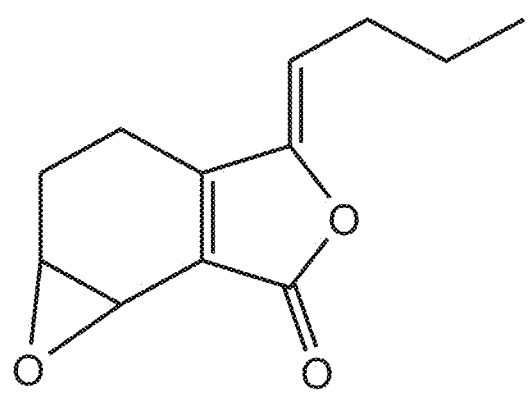

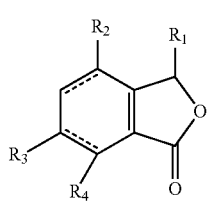

wherein $R_1$ is $C_2$-$C_6$ alkyl, $C_2$-$C_6$ alkenyl or $C_2$-$C_6$ alkenol group; $R_2$ is one or more H or OH; and $R_3$ and $R_4$ are each independent H or OH or both of them combine together to form an epoxy group. The example of Formula I is Z-butylidenephthalide (shown in FIG. 1a), Z-ligustilide (shown in FIG. 1b), senkyunolide A (shown in FIG. 1c), senkyunolide H (shown in FIG. 1d), senkyunolide I (shown in FIG. 1e), senkyunolide F (shown in FIG. 1f), E-butylidenephthalide (shown in FIG. 1g), E-ligustilide (shown in FIG. 1h), 3-butylphthalide (shown in FIG. 1i), 3-butylidene-4-hydrophthalide (shown in FIG. 1j), 6,7-dihydroxyligustilide (shown in FIG. 1k), or 6,7-epoxyligustilide (shown in FIG. 1l). The compound of Formula I can be a compound synthesized via organic synthesis approaches. Alternatively, the compound of Formula I can also be a natural compound extracted from herbs, such as, but not limited to, *Angelica sinensis* (Oliv.) Diels or *Ligusticum chuanxiong* Hort.

Besides, the compound of Formula I can be used to combine with any of other compounds stabilizing the oxygenated hemoglobin, hemoglobin variants, recombinant hemoglobin and hemoglobin-based blood substitute, in the low oxygen affinity "T" state. For example, the compound of Formula I can be used as a medication further comprising ferulic acid, while mole fractions of the compound of Formula I and ferulic acid of the medication are 0.05-0.95 and 0.05-0.95, respectively. The compound of Formula I and ferulic acid can form hydrogen bonds at the α1/α2 interface of hemoglobin, hemoglobin variants, recombinant hemoglobin and hemoglobin-based blood substitute, strengthening the α1/α2 interface of hemoglobin, hemoglobin variants, recombinant hemoglobin and hemoglobin-based blood substitute, therefore stabilizing the oxygenated hemoglobin, hemoglobin variants, recombinant hemoglobin and hemoglobin-based blood substitute in the low oxygen affinity "T" state and facilitating the oxygen release to the organs and the peripheral tissues.

Moreover, the medication can further comprise 2,3-bisphosphoglycerate in a mole fraction at most equal to 0.45 of the medication. The compound of Formula I, ferulic acid and 2,3-bisphosphoglycerate can form hydrogen bonds with αArg141, αVal1, βHis143 and βLys82 of hemoglobin, respectively, strengthening the α1/α2 interface and β1/β2 cavity of hemoglobin. Therefore, the medication further comprising 2,3-bisphosphoglycerate can also stabilize the oxygenated hemoglobin in the low oxygen affinity "T" state and facilitate the oxygen release to the organs and the peripheral tissues.

Furthermore, the medication can be used as the medical functional substitute of 2,3-bisphosphoglycerate to facilitate the oxygen release to organs and peripheral tissues for hemoglobin variants, hemoglobin recombinants and hemoglobin-based blood substitute which lack the capability to bind with 2,3-bisphosphoglycerate. For instance, the fetal hemoglobin ($α_2γ_2$, HbF) is a hemoglobin variant and also a potential hemoglobin-based blood substitute, which has been proposed to treat certain blood diseases, such as sickle cell diseases and β-thalassemia. However, the inability of fetal hemoglobin to bind with 2,3-bisphosphoglycerate makes it less efficient in releasing oxygen than the normal hemoglobin. By stabilizing the low oxygen affinity T state of the fetal hemoglobin via its $α_1/α_2$ interface, the medication can be used to promote the oxygen release capability of the fetal hemoglobin, allowing it to act as a better functional blood substitute.

In the present invention, the compound of Formula I of the invention can be given to any target individually or combined with any acceptable excipients, for example drug carriers or other ingredients, and is capable of being further manufactured into any form of medicaments, including, but not limited to, oral administration, intravenous injection, intravenous infusion and nasal inhalation for effective delivery to the targets. For the oral administration, the compound of Formula I of the invention can be manufactured into the form of pill, capsule, powder, solution and pastil. The dosage of the medicaments depends on the form of medicaments, the bioavailability of the corresponding form of medicaments and the medical conditions of individuals. The suggested dosage of the compound of Formula I is 5-100 mg/kg body weight per day.

In order to evaluate the effect of the compound of Formula I on stabilizing the oxygenated hemoglobin in the low oxygen affinity "T" state, compounds including 2,3-bisphosphoglycerate (group A0), Z-butylidenephthalide (group A1), Z-ligustilide (group A2), senkyunolide A (group A3), senkyunolide H (group A4) and senkyunolide I (group A5) are mixed with hemoglobin as a function of their mole ratio to hemoglobin, followed by the resonance Raman spectroscopy measurements at 532 nm excitation wavelength under the oxygen atmosphere. The percentages of the high oxygen affinity "R" state for hemoglobin treated with 2,3-bisphosphoglycerate (shown in FIG. 2a, as reference) and various phthalide phyto-compounds (shown in FIGS. 2b to 2f) are analyzed from the resonance Raman spectroscopy measurements. In more specific, the percentage of high oxygen affinity "R" state for each treated hemoglobin was obtained by fitting a simulated spectrum comprised of adjustable weighing factors of the T and R states of pure hemoglobin to the obtained resonance Raman spectrum of treated hemoglobin.

Figure 2A:
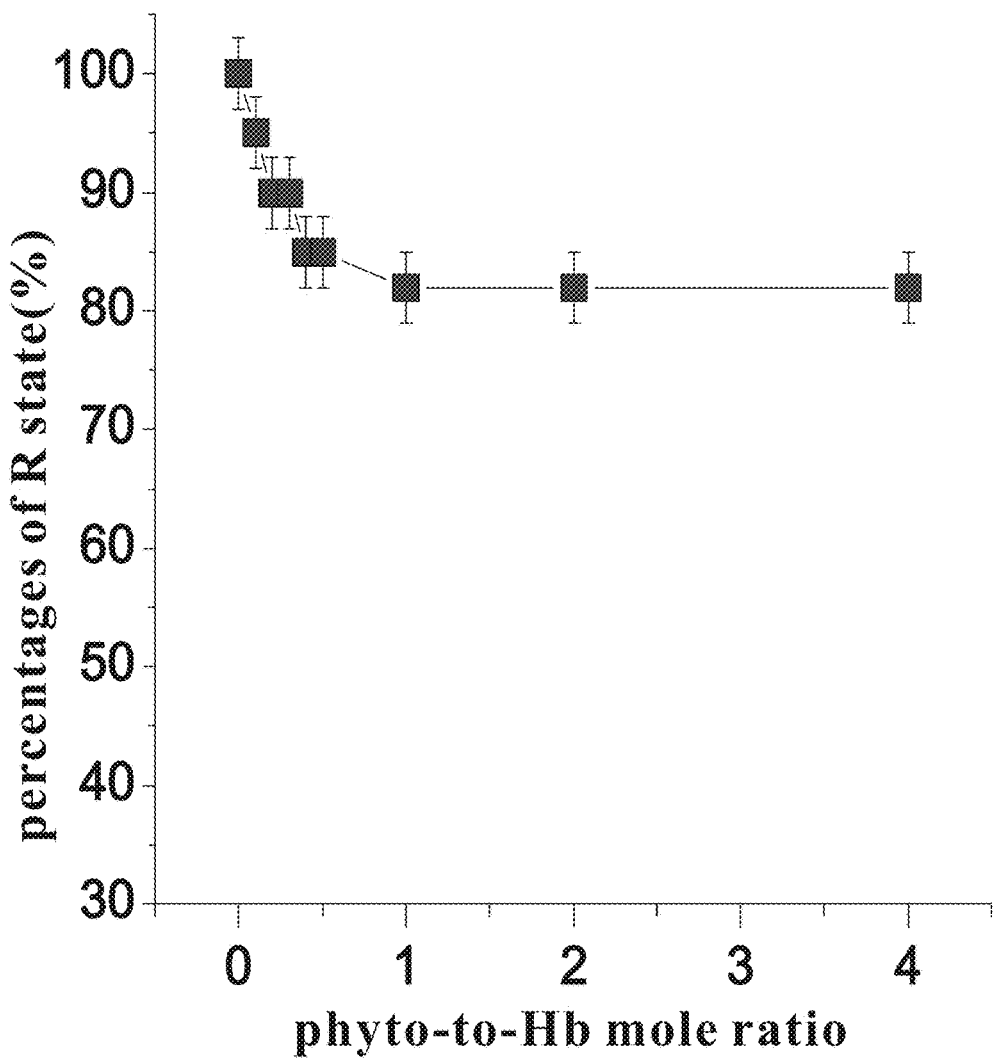
FIG. 2a is a diagram illustrating the suppression of the "R" state for the oxygenated hemoglobin treated with varying mole ratios of 2,3-bisphosphoglycerate to hemoglobin tetramer.
Figure 2B:
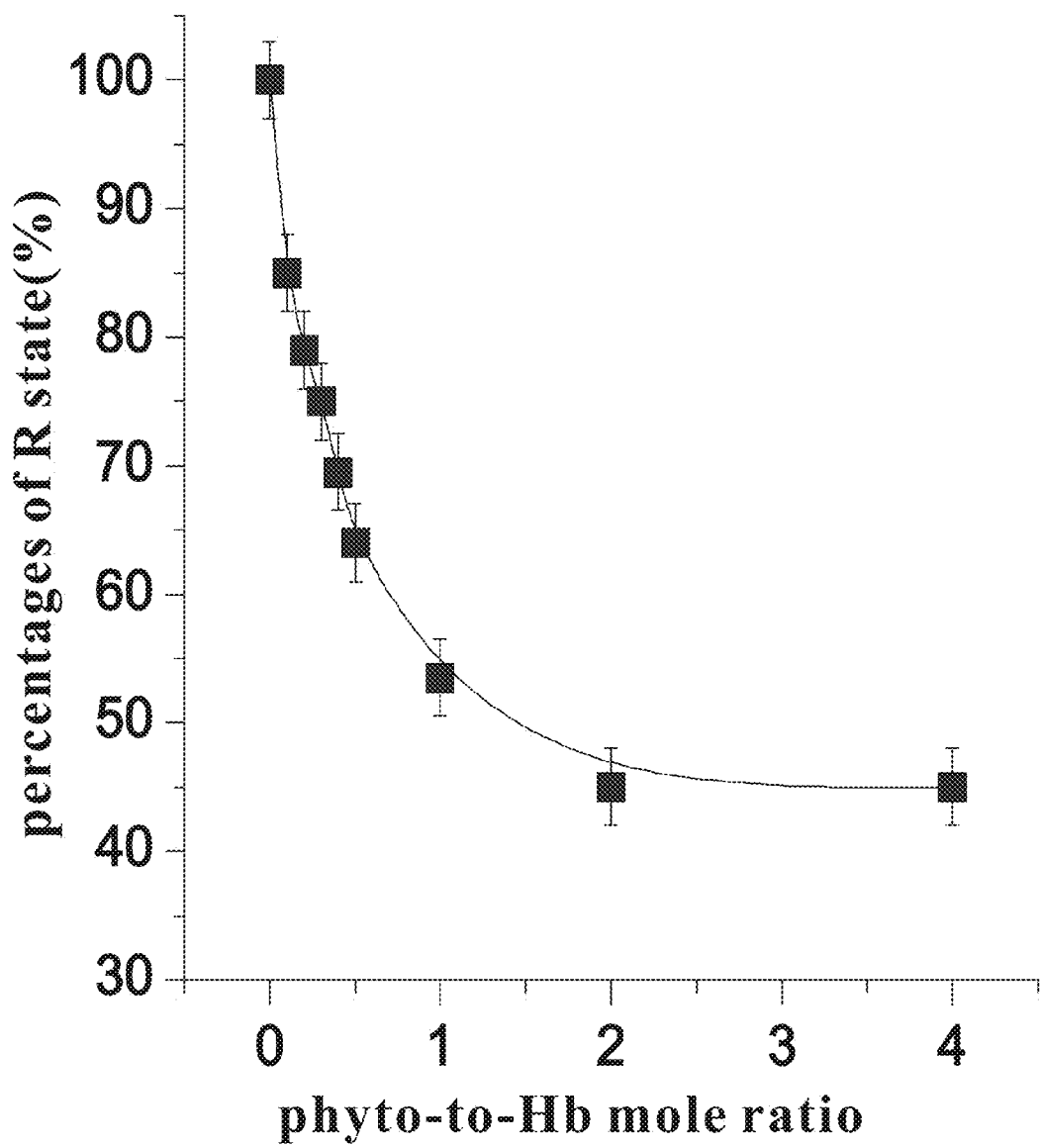
FIG. 2b is a diagram illustrating the suppression of the "R" state for the oxygenated hemoglobin treated with varying mole ratios of Z-butylidenephthalide of the invention to hemoglobin tetramer.
Figure 2C:
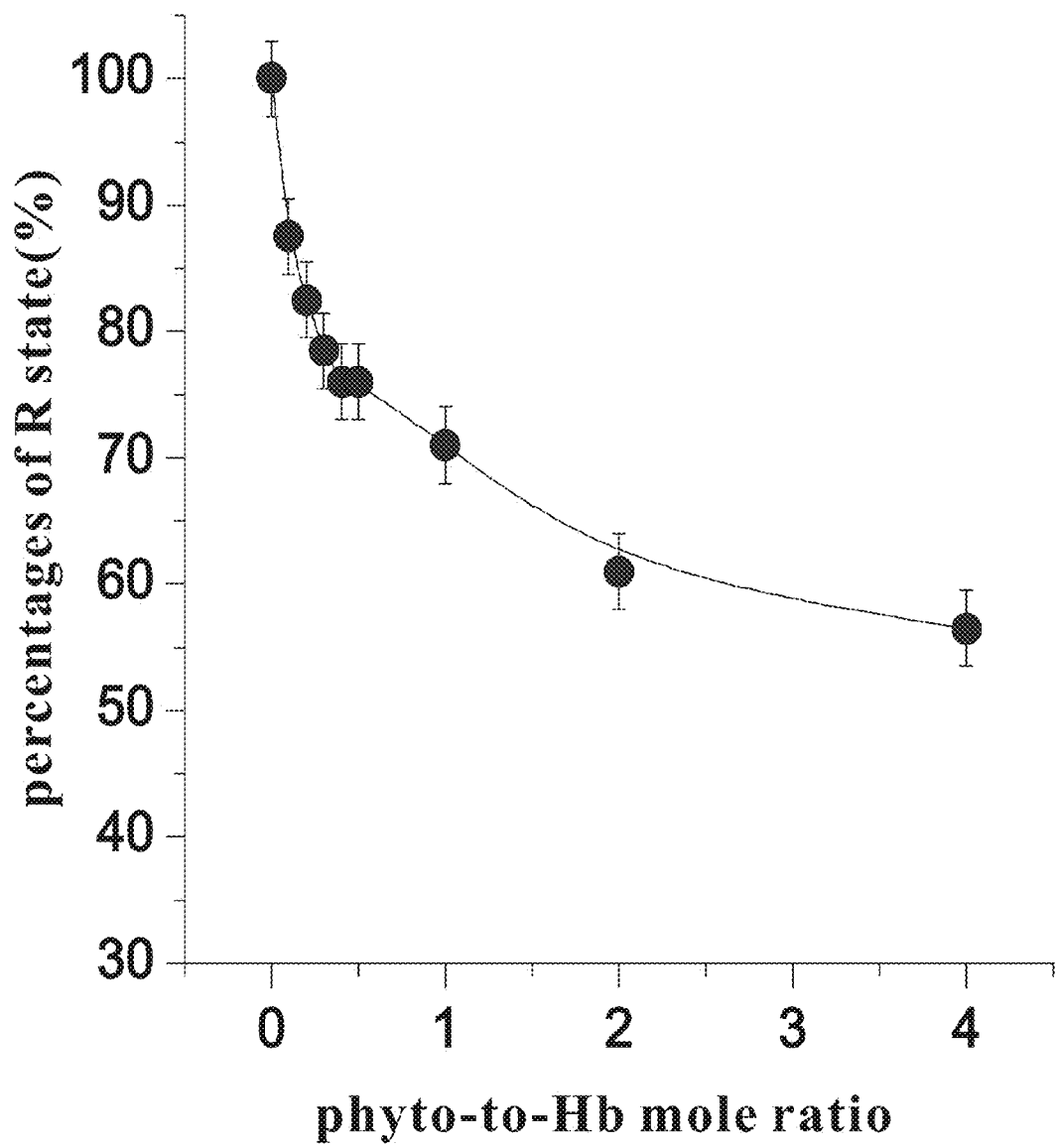
FIG. 2c is a diagram illustrating the suppression of the "R" state for the oxygenated hemoglobin treated with varying mole ratios of Z-ligustilide of the invention to hemoglobin tetramer.
Figure 2D:
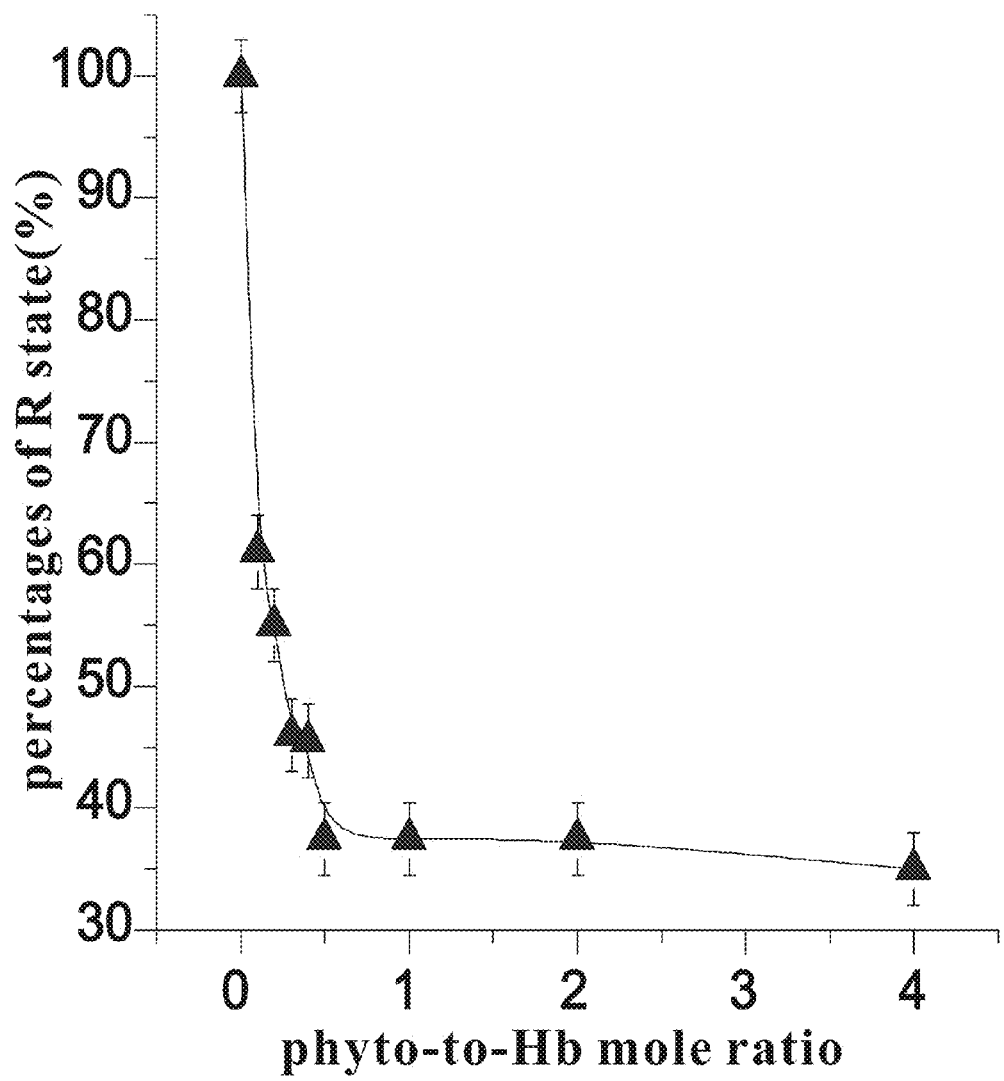
FIG. 2d is a diagram illustrating the suppression of the "R" state for the oxygenated hemoglobin treated with varying mole ratios of senkyunolide A of the invention to hemoglobin tetramer.
Figure 2E:
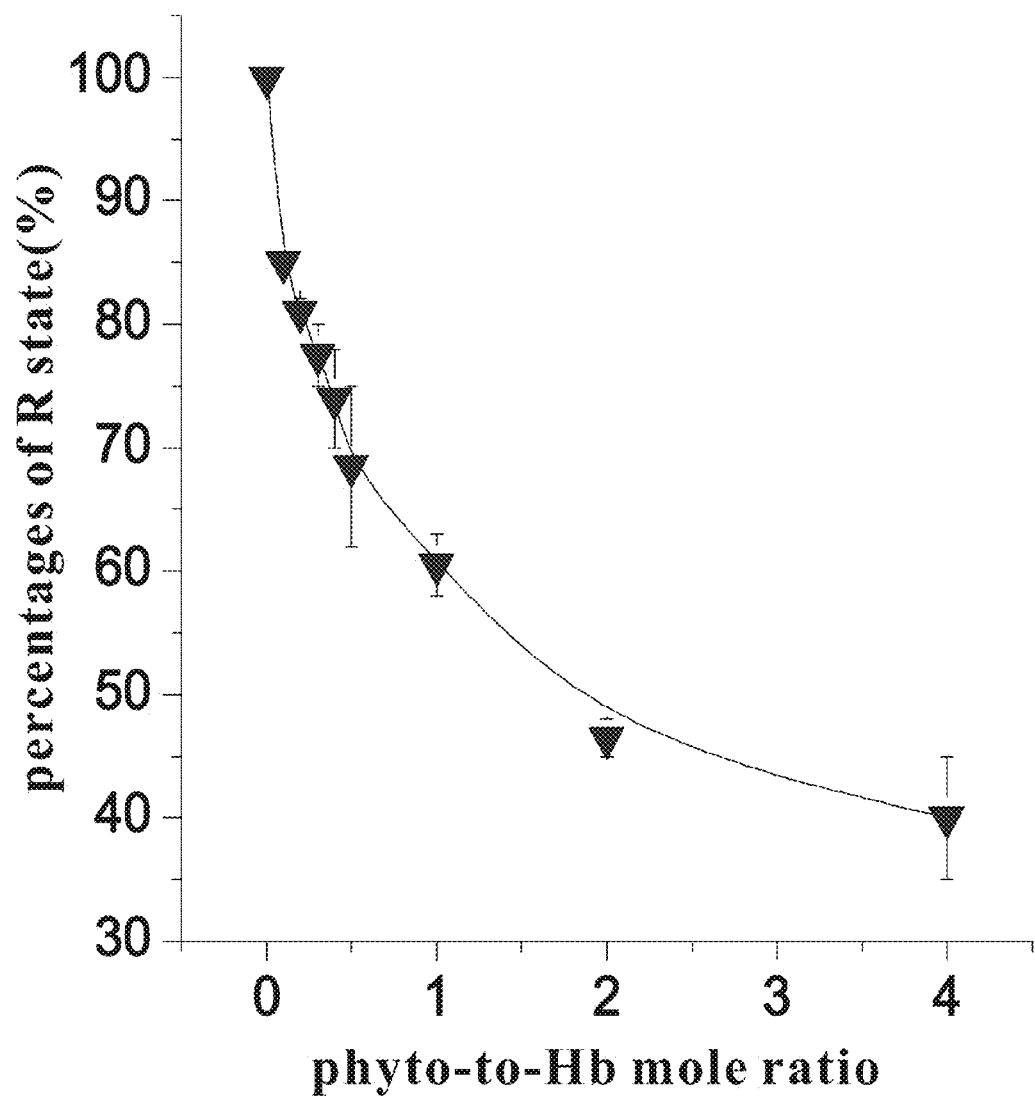
FIG. 2e is a diagram illustrating the suppression of the "R" state for the oxygenated hemoglobin treated with varying mole ratios of senkyunolide H of the invention to hemoglobin tetramer.
Figure 2F:
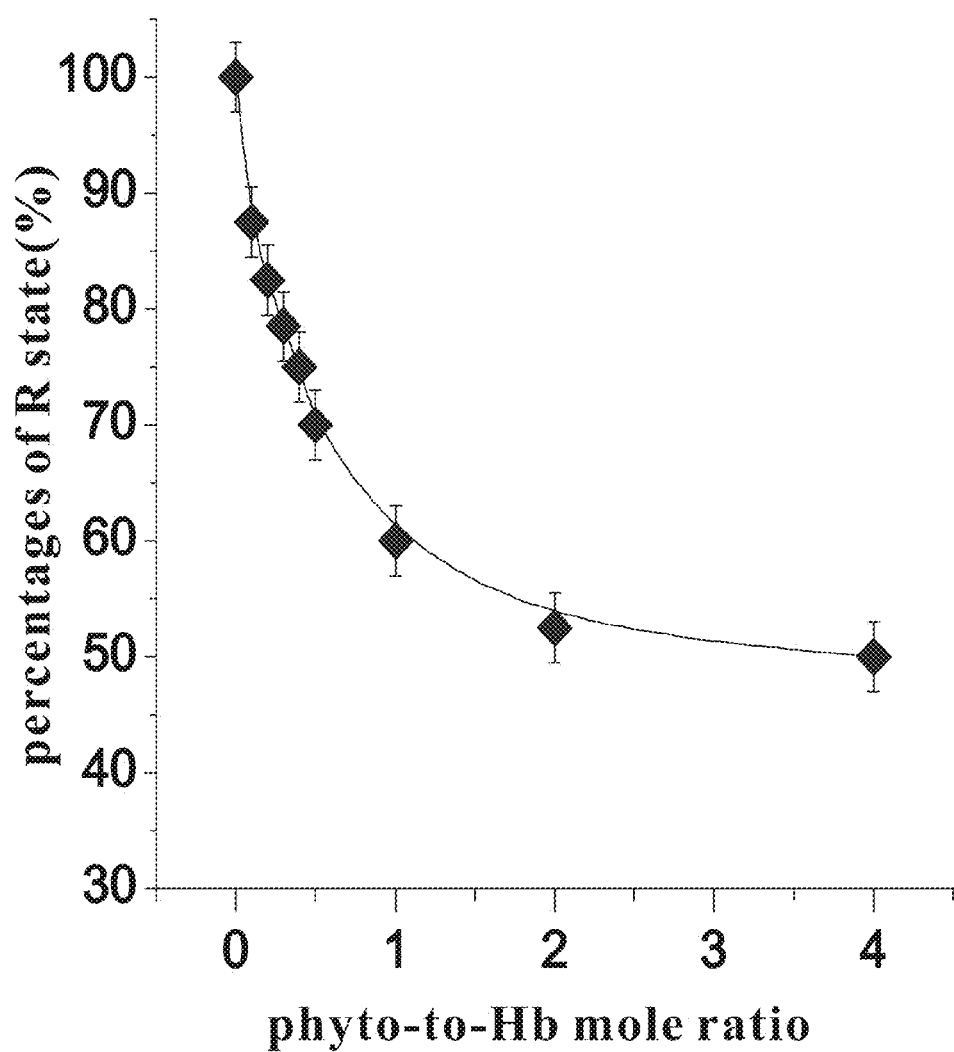
FIG. 2f is a diagram illustrating the suppression of the "R" state for the oxygenated hemoglobin treated with varying mole ratios of senkyunolide I of the invention to hemoglobin tetramer.

Referring to FIG. 2a, 2,3-bisphosphoglycerate of group A0 reduces the relative ratio of the high oxygen affinity "R" state for oxygenated hemoglobin, demonstrating that 2,3-bisphosphoglycerate stabilizes the low oxygen affinity "T" state and inhibits the transformation from the low oxygen affinity "T" state to the high oxygen affinity "R" state, with the "R" state suppression efficiency of about 20%. Moreover, referring to FIGS. 2b to 2f, each of the phthalide compounds, including Z-butylidenephthalide (FIG. 2b), Z-ligustilide (FIG. 2c), senkyunolide A (FIG. 2d), senkyunolide H (FIG. 2e) and senkyunolide I (FIG. 2f) can also stabilize the low oxygen affinity "T" state and inhibit its transformation from the low oxygen affinity "T" state to the high oxygen affinity "R" state with the "R" state suppression efficiency higher than 20% shown in FIG. 2a (group A0).

In order to evaluate the effect of the compound of phthalides on stabilizing the oxygenated hemoglobin variants in the low oxygen affinity "T" state, compounds including 2,3-bisphosphoglycerate (group A0), Z-butylidenephthalide (group A1), Z-ligustilide (group A2), senkyunolide A (group A3), senkyunolide H (group A4) and senkyunolide I (group A5) are mixed with fetal hemoglobin ($\alpha_2\gamma_2$, HbF) as a representative hemoglobin variant which is also a potential hemoglobin-based blood substitute, followed by the resonance Raman spectroscopy measurements under the oxygen atmosphere. The percentages of the high oxygen affinity "R" state of fetal hemoglobin treated with 2,3-bisphosphoglycerate (shown in FIG. 3a) and various phthalide phyto-compounds (shown in FIGS. 3b to 3f) are also analyzed from the resonance Raman spectroscopy measurements, following the same spectral analysis procedures as that of normal hemoglobin.

Figure 3A:
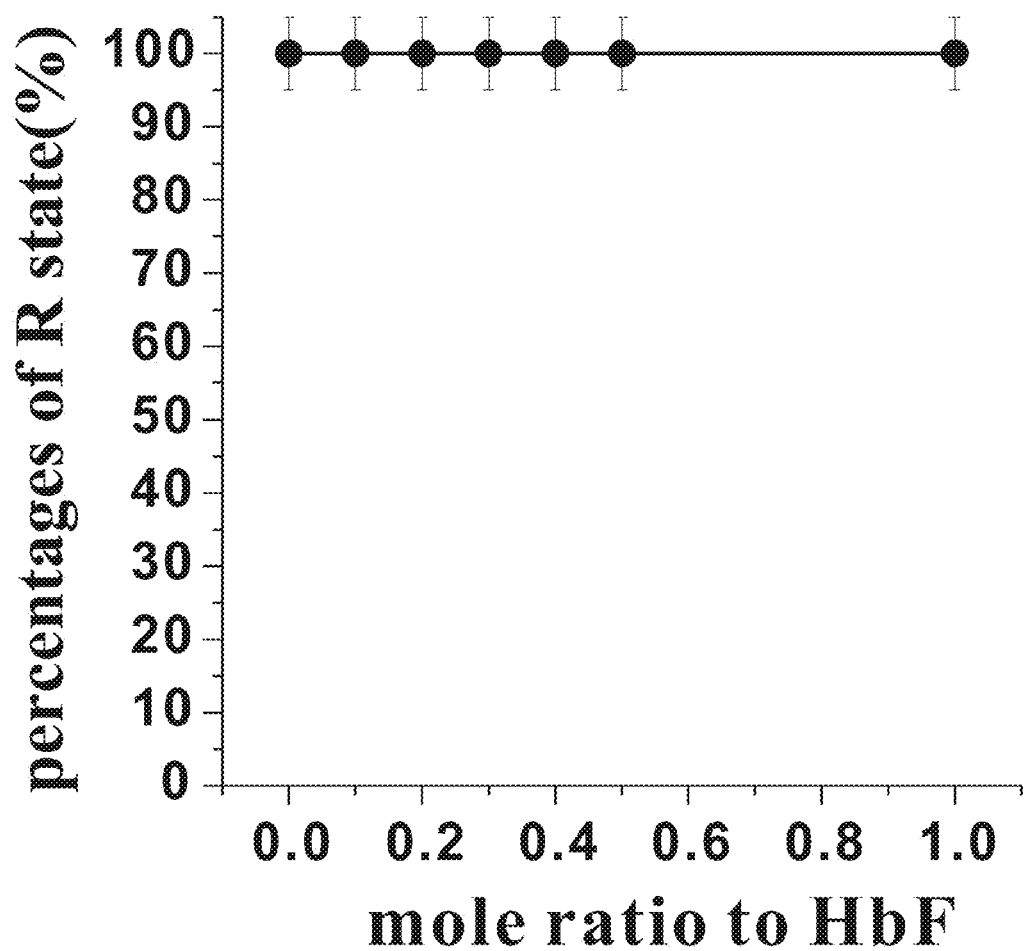
FIG. 3a is a diagram illustrating the suppression of the "R" state for the oxygenated fetal hemoglobin treated with varying mole ratios of 2,3-bisphosphoglycerate to hemoglobin tetramer.
Figure 3B:
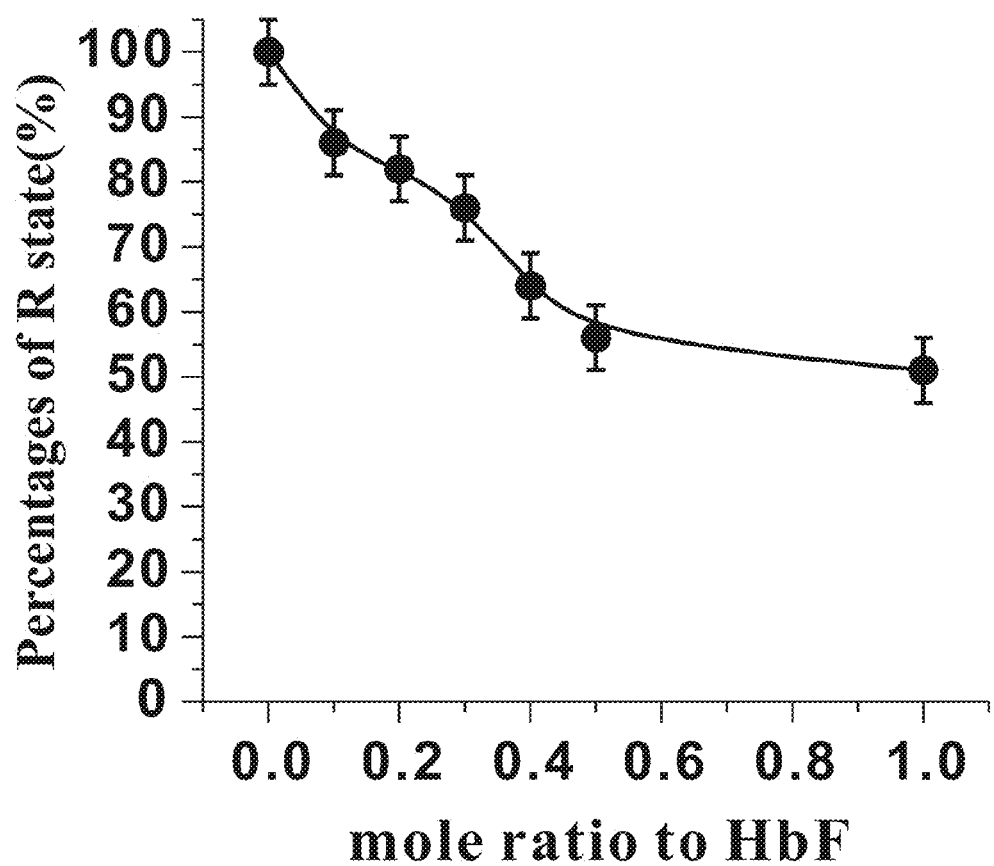
FIG. 3b is a diagram illustrating the suppression of the "R" state for the oxygenated fetal hemoglobin treated with varying mole ratios of Z-butylidenephthalide of the invention to hemoglobin tetramer.
Figure 3C:
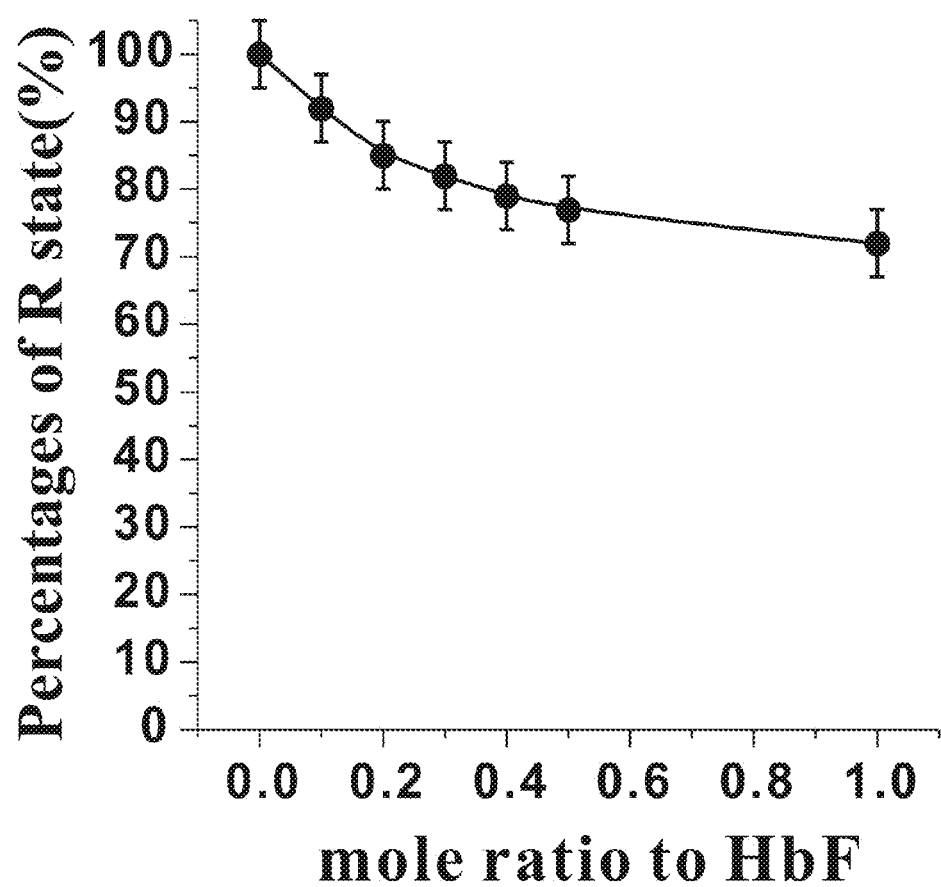
FIG. 3c is a diagram illustrating the suppression of the "R" state for the oxygenated fetal hemoglobin treated with varying mole ratios of Z-ligustilide of the invention to hemoglobin tetramer.
Figure 3D:
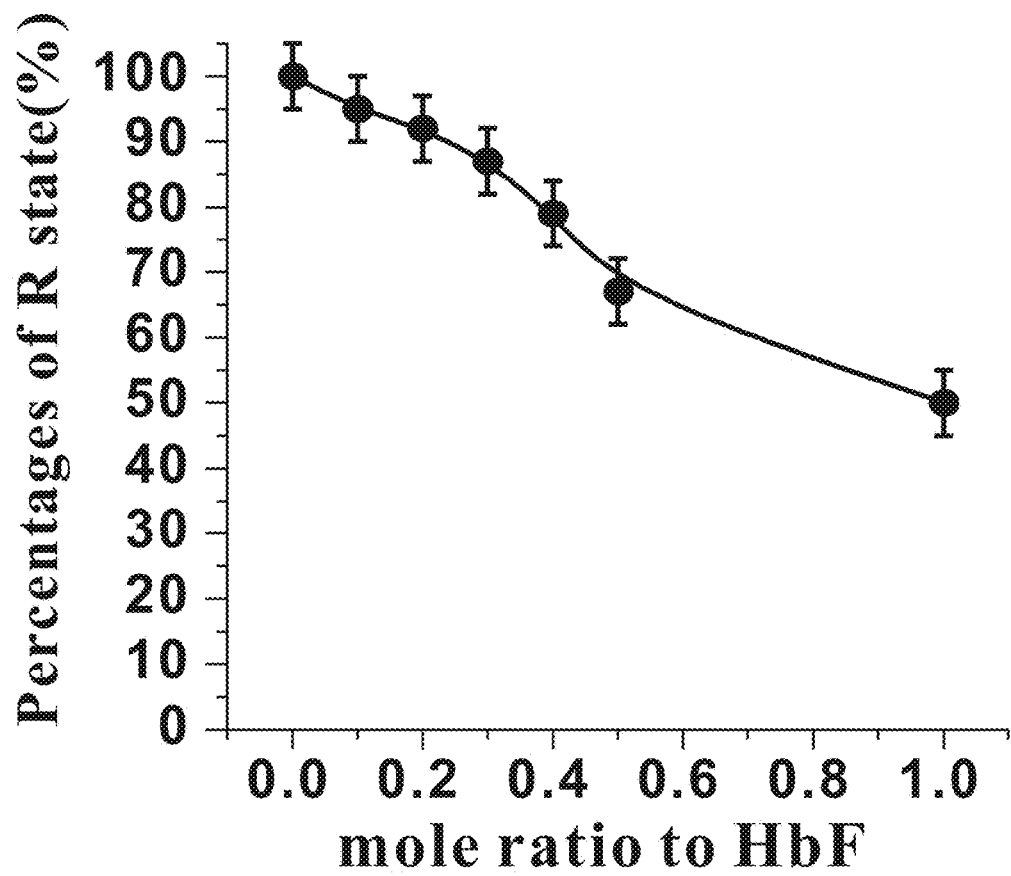
FIG. 3d is a diagram illustrating the suppression of the "R" state for the oxygenated fetal hemoglobin treated with varying mole ratios of senkyunolide A of the invention to hemoglobin tetramer.
Figure 3E:
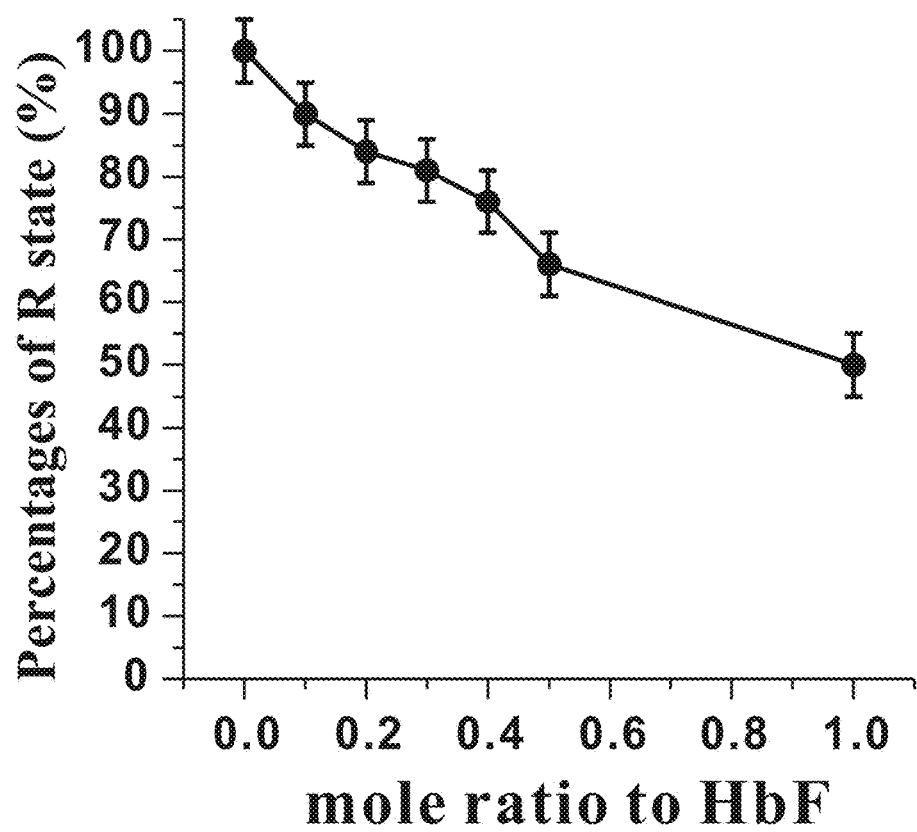
FIG. 3e is a diagram illustrating the suppression of the "R" state for the oxygenated fetal hemoglobin treated with varying mole ratios of senkyunolide H of the invention to hemoglobin tetramer.
Figure 3F:
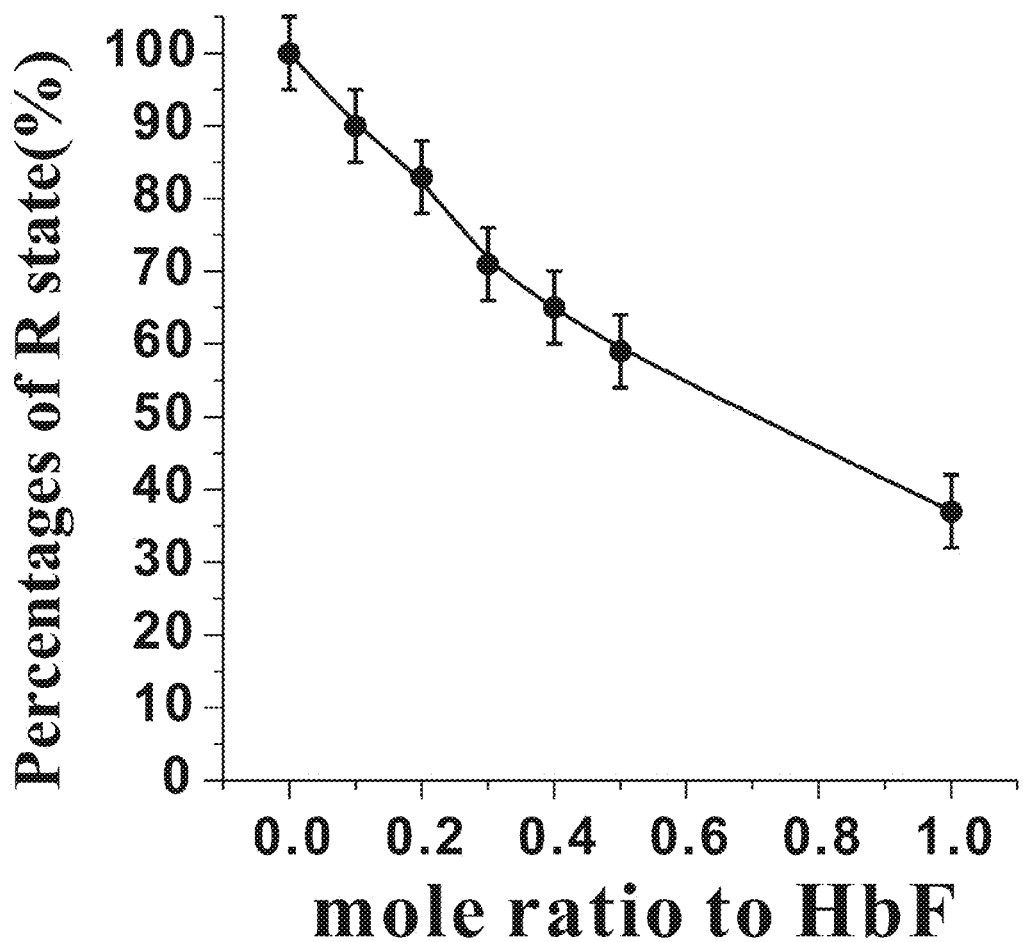
FIG. 3f is a diagram illustrating the suppression of the "R" state for the oxygenated fetal hemoglobin treated with varying mole ratios of senkyunolide I of the invention to hemoglobin tetramer.

Referring to FIG. 3a, 2,3-bisphosphoglycerate of group A0 exhibits no effect in lowering the relative ratio of the high oxygen affinity "R" state of fetal hemoglobin, demonstrating that 2,3-bisphosphoglycerate is incapable of facilitating the oxygen release for fetal hemoglobin due to the inability of fetal hemoglobin to interact with 2,3-bisphosphoglycerate, as expected. In contrast, referring to FIGS. 3b to 3f, each of the compounds of phthalides including Z-butylidenephthalide (FIG. 3b), Z-ligustilide (FIG. 3c), senkyunolide A (FIG. 3d), senkyunolide H (FIG. 3e) and senkyunolide I (FIG. 3f) can stabilize the low oxygen affinity "T" state for the oxygenated fetal hemoglobin under the oxygen atmosphere and inhibit its transformation from the low oxygen affinity "T" state to the high oxygen affinity "R" state, demonstrating the allosteric regulating ability of the medication of this invention in stabilizing the low affinity "T" state, thus facilitating the oxygen release for fetal hemoglobin, and in more general for hemoglobin variants, recombinant hemoglobin and hemoglobin-based blood substitutes whose composition commonly retain two $\alpha$ subunits, and thus an $\alpha1/\alpha2$ subunit interface.

Figure 4A:
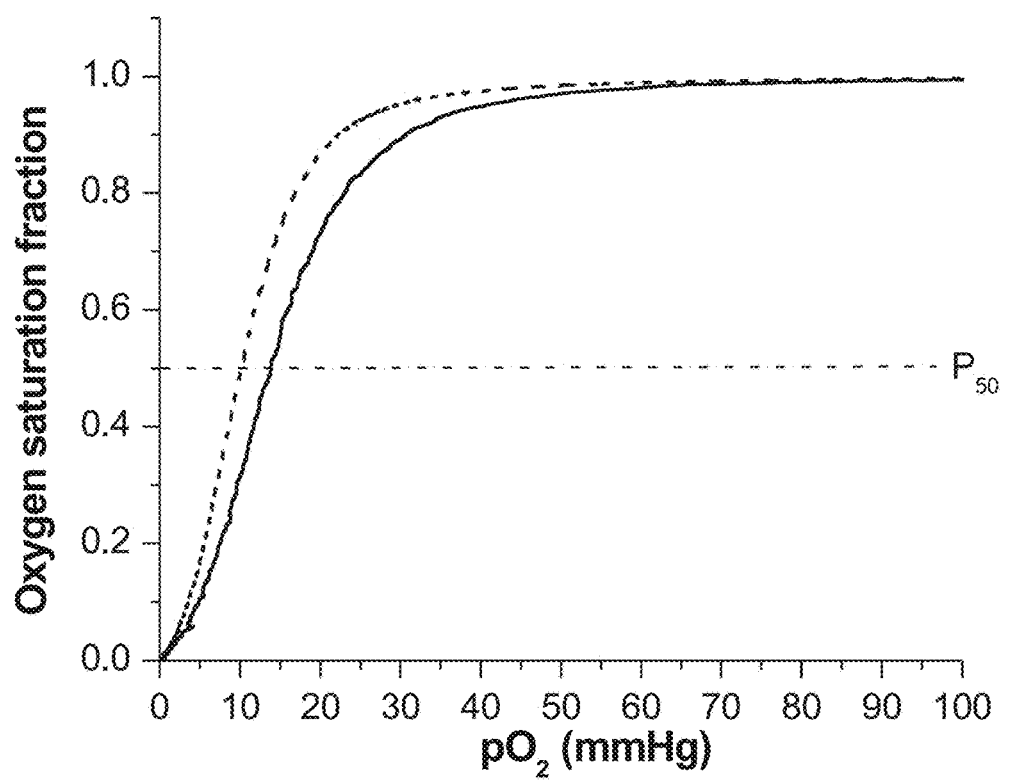
FIG. 4a is a diagram illustrating the oxygen equilibrium curve (OEC) of hemoglobin treated with 2,3-bisphosphoglycerate with a molar ratio to Hb of 1.0 (dash black curve). The OEC of pure hemoglobin (solid black curve) is also shown as the reference. The $P_{50}$ value derived from the OEC for pure hemoglobin and for Hb treated with 2,3-bisphosphoglycerate are 12.6 and 16.4±1 mmHg, respectively.
Figure 4B:
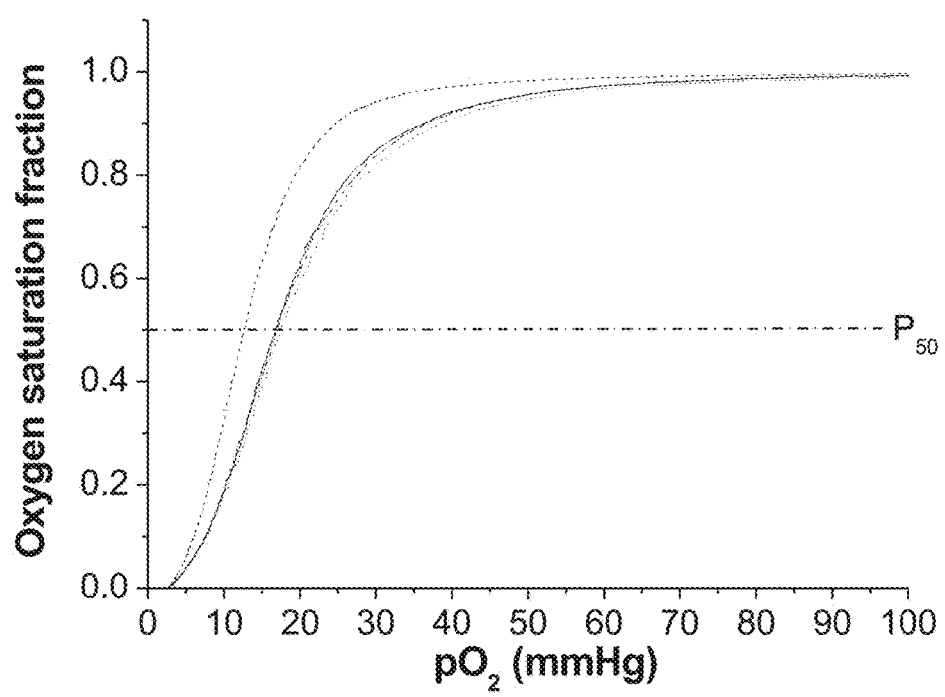
FIG. 4b is a diagram illustrating the oxygen equilibrium curve (OEC) of hemoglobin treated with Z-butylidenephthalide of the invention at varying levels of treatments, with the molar ratio of Z-butylidenephthalide to Hb of: 0.2 (solid black curve), 0.5 (dash-dot black curve) and 0.8 (dot black curve). The OEC of pure hemoglobin (dash black curve) is also shown as the reference.

To evaluate the effect of the compound of phthalides on reducing the oxygen affinity and thus promoting the oxygen release, the oxygen equilibrium curves (OEC) for hemoglobin treated with 2,3-bisphosphoglycerate (solid black curve in FIG. 4a) and Z-butylidenephthalide (Z-butylidenephthalide-to-Hb molar ratio of: 0.2, solid black curve; 0.5, dash-dot black curve; 0.8, dot black curve in FIG. 4b), are measured in comparison with that of pure hemoglobin (dash black curves in FIGS. 4a and 4b).

Figure 5A:
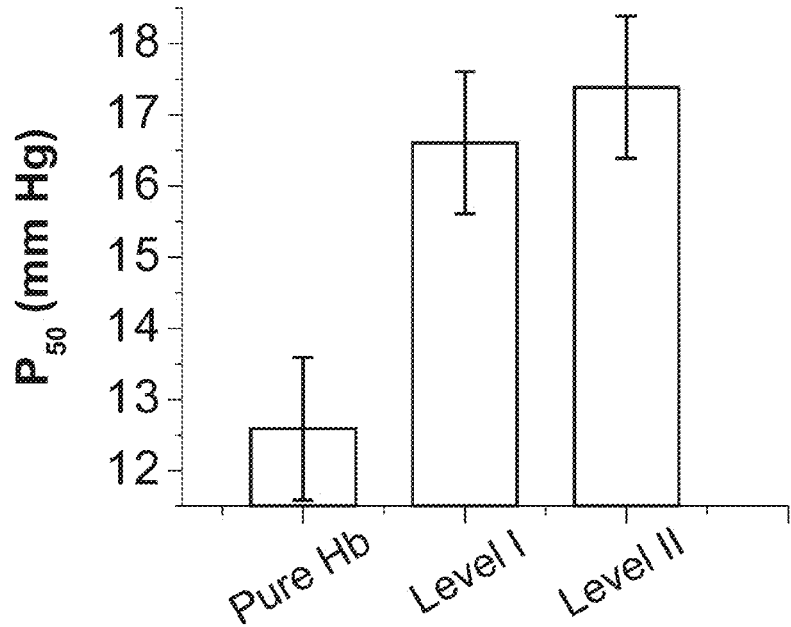
FIG. 5a is a diagram illustrating the $P_{50}$ value of hemoglobin treated with Z-butylidenephthalide of the invention at two varying extents of treatment, including the molar ratio of Z-butylidenephthalide to Hb of: 0.2 (Level I) and 0.8 (Level II). The $P_{50}$ for pure Hb is also shown in each panel as the reference.
Figure 5B:
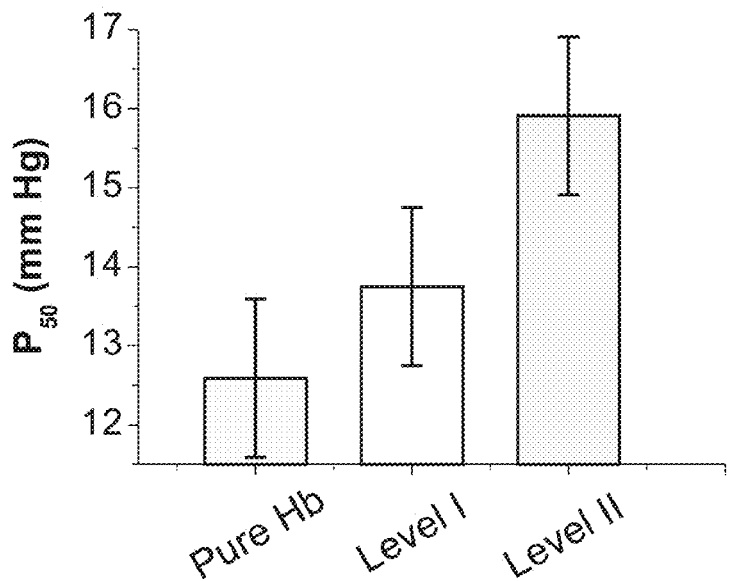
FIG. 5b is a diagram illustrating the $P_{50}$ value of hemoglobin treated with Z-ligustilide of the invention at two varying extents of treatment, including the molar ratio of Z-ligustilide to Hb of: 0.2 (Level I) and 0.8 (Level II). The $P_{50}$ for pure Hb is also shown in each panel as the reference.
Figure 5C:
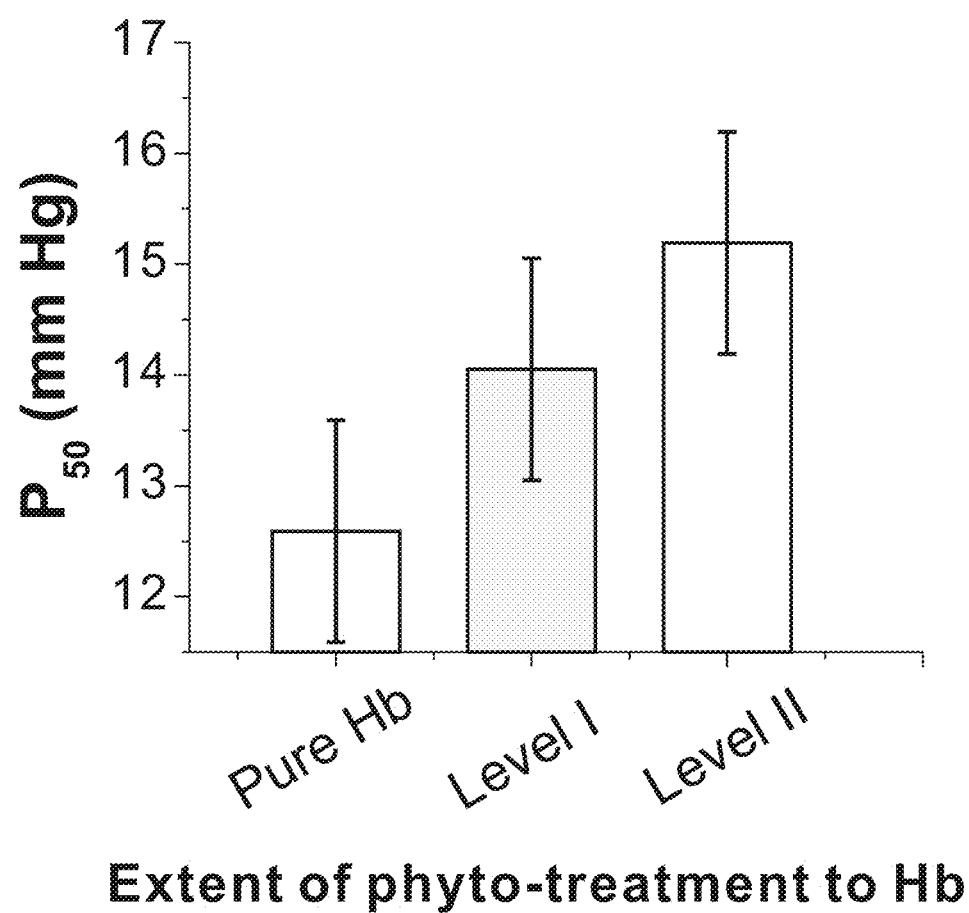
FIG. 5c is a diagram illustrating the $P_{50}$ value of hemoglobin treated with senkyunolide A of the invention at two varying extents of treatment, including the molar ratio of senkyunolide A to Hb of: 0.2 (Level I) and 0.8 (Level II). The $P_{50}$ for pure Hb is also shown in each panel as the reference.

From the oxygen equilibrium measurements, the $P_{50}$ values of hemoglobin treated compounds, including Z-butylidenephthalide, Z-ligustilide and senkyunolide A are obtained, as shown in FIGS. 5a to 5c. $P_{50}$, defined as the oxygen partial pressure required for 50% of Hb to become oxygenated or deoxygenated, is a direct measure of oxygen affinity for hemoglobin, which increases with decreasing oxygen affinity. At the effector-to-Hb mole ratio of 0.8 (Level II in FIGS. 5a to 5c), the $P_{50}$ values for Hb treated with Z-butylidenephthalide, Z-ligustilide, and senkyunolide I were found to be 17.4, 15.9 and 15.2±1 mmHg respectively, while the $P_{50}$ is 12.6±1 mmHg for pure hemoglobin without additional treatments, confirming that the compound of phthalides leads to an oxygen affinity reduction for hemoglobin, which further indicates that the oxygen molecules can be more efficiently released upon the phthalide treatment of Hb.

In addition, the active sites of oxygenated hemoglobin are analyzed by the computational docking analysis. Referring to TABLE 1, all of the compounds of phthalides including Z-butylidenephthalide (group A1), Z-ligustilide (group A2), senkyunolide A (group A3), senkyunolide H (group A4) and senkyunolide I (group A5) form at least one hydrogen bond with $\alpha$Arg141 of hemoglobin. Moreover, senkyunolide A (group A3), senkyunolide H (group A4) and senkyunolide I (group A5) can form two hydrogen bonds with $\alpha$Arg141 of hemoglobin. By doing so, the compound of phthalides can aid to stabilize the key inter-subunit hydrogen bond between $\alpha_1$Arg141 and $\alpha_2$Lys127 (and/or symmetrically, between $\alpha_1$Lys127 and $\alpha_2$Arg141) of hemoglobin at the $\alpha1/\alpha2$ interface of hemoglobin, thus stabilizing the oxygenated hemoglobin in the low oxygen affinity "T" state and facilitating the oxygen release to the organs and the peripheral tissues. Furthermore, since most hemoglobin variants, recombinant hemoglobin and hemoglobin-based blood substitute retain the identical $\alpha$ subunit pair and the $\alpha1/\alpha2$ interface as that of normal hemoglobin, the above-described operation principle of phthalides compounds in stabilizing the "T" state via the $\alpha1/\alpha2$ interface and thus facilitating the oxygen release to organs and peripheral tissues also apply to hemoglobin variants, recombinant hemoglobin and hemoglobin-based blood substitutes that contains two identical α subunits as that of normal hemoglobin.

TABLE 1

| Groups | Compounds | Active sites[1] | Bond distance (Å) |
|---|---|---|---|
| A1 | Z-butylidenephthalide | $\alpha_1$Arg141 | 1.808 |
| A2 | Z-ligustilide | $\alpha_1$Arg141 | 1.808 |
| A3 | Senkyunolide A | $\alpha_1$Arg141 | 1.934 |
|  |  | $\alpha_1$Arg141 | 2.123 |
| A4 | Senkyunolide H | $\alpha_1$Arg141 | 1.955 |
|  |  | $\alpha_1$Arg141 | 2.155 |
|  |  | $\alpha_1$Arg141 | 2.360 |
|  |  | $\alpha_2$Ser102 | 1.633 |
|  |  | $\alpha_2$Ser133 | 1.754 |
| A5 | Senkyunolide I | $\alpha_1$Arg141 | 1.954 |
|  |  | $\alpha_1$Arg141 | 2.041 |
|  |  | $\alpha_2$Ser131 | 1.715 |
|  |  | $\alpha_2$Thr134 | 2.137 |

[1]Because of the same molecular structure between α1 and α2 subunits, the words "$\alpha_1$" and "$\alpha_2$" are only used to positively recite the active sites on the different α subunits. That is, the compound Z-butylidenephthalide, which has an active site on α1Arg141, can also act on its symmetric counterpart, α2Arg141. The similar results can be observed in other compounds of phthalides.

Moreover, referring to TABLE 2, all of the compounds of phthalides including the compounds of phthalides including senkyunolide F (group B1), E-butylidenephthalide (group B2), E-ligustilide (group B3), 3-butylphthalide (group B4), 3-butylidene-4-hydrophthalide (group B5), 6,7-dihydroxyligustilide (group B6) and 6,7-epoxyligustilide (group B7) form at least one hydrogen bond between αArg141 of hemoglobin, as analyzed by the computational docking analysis, whereas 3-butylphthalide (group B4) and 3-butylidene-4-hydrophthalide (group B5) can form at least two hydrogen bonds with αArg141 of hemoglobin. These compounds of phthalides can also stabilize the oxygenated hemoglobin in the low oxygen affinity "T" state and facilitate the oxygen release to the organs and the peripheral tissues.

TABLE 2

| Groups | Compounds | Active sites[1] | Bond distance (Å) |
|---|---|---|---|
| B1 | Senkyunolide F | $\alpha_1$ Arg141 | 1.990 |
|  |  | $\alpha_2$ Val1 | 2.184 |
| B2 | E-butylidenephthalide | $\alpha_1$ Arg141 | 1.820 |
|  |  | $\alpha_2$ Val1 | 2.210 |
| B3 | E-ligustilide | $\alpha_1$ Arg141 | 2.210 |
|  |  | $\alpha_2$ Val1 | 1.820 |
| B4 | 3-butylphthalide | $\alpha_1$ Arg141 | 2.011 |
|  |  | $\alpha_1$ Arg141 | 2.048 |
| B5 | 3-butylidene-4-hydrophthalide | $\alpha_1$ Arg141 | 1.730 |
|  |  | $\alpha_1$ Arg141 | 1.954 |
|  |  | $\alpha_1$ Thr137 | 2.048 |
| B6 | 6,7-dihydroxyligustilide | $\alpha_1$ Arg141 | 2.248 |
|  |  | $\alpha_2$ Val1 | 1.834 |
|  |  | $\alpha_2$ Val1 | 1.964 |
|  |  | $\alpha_2$ Lys127 | 2.107 |
| B7 | 6,7-epoxyligustilide | $\alpha_1$ Arg141 | 2.102 |

[1]Because of the same molecular structure between α1 and α2 subunits, the words "$\alpha_1$" and "$\alpha_2$" are only used to positively recite the active sites on the different α subunits. That is, the compound Z-butylidenephthalide, which has an active site on α1Arg141, can also act on its symmetric counterpart, α2Arg141. The similar results can be observed in other compounds of phthalides.

In conclusion, the compound of phthalides according to the invention can form at least one hydrogen bonds with αArg141 of hemoglobin, hemoglobin variants, recombinant hemoglobin and hemoglobin-based blood substitutes, stabilizing the oxygenated hemoglobin, hemoglobin variants, recombinant hemoglobin and hemoglobin-based blood substitutes in the low oxygen affinity "T" state and thus facilitating the oxygen release to the organs and the peripheral tissues. Therefore, the compound of phthalides according to the invention can be used for improving the oxygen-releasing ability of hemoglobin to the organs and the peripheral tissues in human bodies, and further improving conditions or diseases caused by anoxia, such as anemia, migraine, dysmenorrhea, hypertension and the corresponding diseases.

Moreover, the compound of phthalides according to the invention can enhance and thus ensure sufficient oxygen uptake, preventing from metabolism abnormality of the organs and the peripheral tissues. Therefore, the compound of phthalides according to the invention poses the therapeutic effects on preventing from structural and functional abnormalities of tissue cells and related biomolecules or growth of carcinogenic cells, and can be further used for protecting from cardiovascular diseases, neurodegenerative diseases and cancers.

Furthermore, the medication according to the invention comprises active substances such as the compound of phthalides and ferulic acid; therefore, it can sequentially form hydrogen bonds with αArg141 and αVal1 of hemoglobin, stabilizing the oxygenated hemoglobin in the low oxygen affinity "T" state and facilitating the oxygen release to the organs and the peripheral tissues. The medication can be used for improving medical conditions or diseases caused by anoxia, such as anemia, migraine, dysmenorrhea, hypertension and the corresponding diseases.

In addition, by ensuring the sufficient oxygen uptake of the organs and the peripheral tissues, the medication according to the invention can also be used for preventing from structural and functional abnormalities of tissue cells and related biomolecules or growth of carcinogenic cells, and can be further used for protecting from cardiovascular diseases, neurodegenerative diseases and cancers.

Furthermore, by stabilizing the low affinity "T" state via the α1/α2 interface, the medication according to the invention can also be used as the medical functional substitute of 2,3-bisphosphoglycerate for hemoglobin variants, recombinant hemoglobin and hemoglobin-based blood substitutes which are incapable of interacting with 2,3-bisphosphoglycerate through the β1/β2 cavity, and therefore can be used to facilitate the oxygen delivery functionality of hemoglobin variants, recombinant hemoglobin and hemoglobin-based blood substitutes.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for improving the oxygen-releasing ability of hemoglobin, hemoglobin variants, recombinant hemoglobin or hemoglobin-based blood substitutes to organs or peripheral tissues in human bodies, by administering a compound of Formula I to a subject in need thereof, wherein the compound of Formula I forms at least one hydrogen bond with αArg141 of hemoglobin, strengthening the α1/α2 interface of hemoglobin, further stabilizing the oxygenated hemoglobin in the low oxygen affinity "T" state and facilitating the oxygen release to the organs or the peripheral tissues,

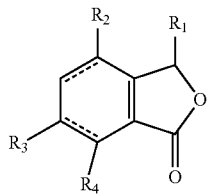

Formula I wherein $R_1$ is $C_2$-$C_6$ alkyl, $C_2$-$C_6$ alkenyl or $C_2$-$C_6$ alkenol group;

$R_2$ is one or more H or OH; and $R_3$ and $R_4$ are each independent H or OH or both of them combine together to form a epoxy group.

2. The method of claim 1, wherein the compound of Formula I is Z-butylidenephthalide.

3. The method of claim 1, wherein the compound of Formula I is Z-ligustilide.

4. The method of claim 1, wherein the compound of Formula I is senkyunolide A.

5. The method of claim 1, wherein the compound of Formula I is senkyunolide H.

6. The method of claim 1, wherein the compound of Formula I is senkyunolide I.

7. The method of claim 1, wherein the compound of Formula I is senkyunolide F.

8. The method of claim 1, wherein the compound of Formula I is E-butylidenephthalide.

9. The method of claim 1, wherein the compound of Formula I is E-ligustilide.

10. The method of claim 1, wherein the compound of Formula I is 3-butylphthalide.

11. The method of claim 1, wherein the compound of Formula I is 3-butylidene-4-hydrophthalide.

12. The method of claim 1, wherein the compound of Formula I is 6,7-dihydroxyligustilide.

13. The method of claim 1, wherein the compound of Formula I is 6,7-epoxyligustilide.

* * * * *